(12) United States Patent
Durduran et al.

(10) Patent No.: US 10,962,414 B2
(45) Date of Patent: Mar. 30, 2021

(54) SPECKLE CONTRAST SYSTEM AND METHOD THAT DISCRIMINATES PHOTONS PATH LENGTHS

(71) Applicants: FUNDACIÓ INSTITUT DE CIÈNCIES FOTÒNIQUES, Castelldefels (ES); INSTITUCIÓ CATALANA DE RECERCA I ESTUDIS AVANÇATS, Barcelona (ES)

(72) Inventors: Turgut Durduran, Castelldefels (ES); Ernesto Vidal Rosas, Castelldefels (ES); Marco Pagliazzi, Castelldefels (ES)

(73) Assignees: FUNDACIÓ INSTITUT DE CIÈNCIES FOTÒNIQUES, CASTELLDEFELS, Barcelona (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 0 days.

(21) Appl. No.: 16/670,207

(22) Filed: Oct. 31, 2019

(65) Prior Publication Data
US 2020/0141798 A1 May 7, 2020

(30) Foreign Application Priority Data
Nov. 2, 2018 (EP) .................................. 18382782

(51) Int. Cl.
*G01J 3/02* (2006.01)
*A61B 5/00* (2006.01)
(Continued)

(52) U.S. Cl.
CPC ............ *G01J 3/027* (2013.01); *A61B 5/0075* (2013.01); *G01B 9/02094* (2013.01); *G01J 3/2889* (2013.01); *A61B 5/0261* (2013.01)

(58) Field of Classification Search
CPC .......... G01N 2021/479; G01B 9/02094; G01B 11/162; G01B 9/02; G03H 1/32; G02B 27/48; A61B 5/026; A61B 5/00
See application file for complete search history.

(56) References Cited

U.S. PATENT DOCUMENTS

| 9,538,926 B2 | 1/2017 | Durduran et al. | |
|---|---|---|---|
| 2008/0287808 A1* | 11/2008 | Tearney | A61B 5/445 600/476 |
| 2010/0081127 A1* | 4/2010 | Maier | A61B 5/0084 435/5 |

OTHER PUBLICATIONS

Bi, R. et al., "Deep tissue flowmetry based on diffuse speckle contrast analysis", Optics Letters, Optical Society of America, vol. 38, No. 9, May 2013, pp. 1401-1403.
(Continued)

*Primary Examiner* — Abdullahi Nur
(74) *Attorney, Agent, or Firm* — Gary J. Gershik; Cooper & Dunham LLP

(57) ABSTRACT

Speckle contrast method and system that discriminates photons based on their path length in tissue, the method comprising the steps of:
  directing light from a pulsed light into a sample by optical elements;
  synchronizing the time between the pulse injection to sample and the detection unit;
  collecting the photons that have travelled through the sample by optics, and conveying the photons of a single or a limited number of speckles from the sample to one or more detection elements;
  time-tagging photons thanks to the synchronization of the detector element and/or the time-tagging electronics with the laser pulse emission;
  estimating each photon time-of-flight by the difference between its time tag and the laser pulse emission;
(Continued)

categorizing the detected photons based on the value of the time-of-flight in a certain number of time gates;
measuring the speckle contrast.

10 Claims, 2 Drawing Sheets

(51) Int. Cl.
    *G01B 9/02*         (2006.01)
    *G01J 3/28*         (2006.01)
    *A61B 5/026*      (2006.01)

(56) References Cited

OTHER PUBLICATIONS

Bi R. et al., "Multi-channel deep tissue flowmetry based on temporal diffuse speckle contrast analysis" Optics Express, vol. 21, No. 19, Sep. 2013, pp. 22854-22861.
Durduran, T. et al., "Diffuse optics for tissue monitoring and tomography", Reports on Progress in Physics, Institute of Physics Publishing, vol. 73, No. 7. Jun. 2010, pp. 1-43.
Valdes, C.P. et al., "Speckle contrast optical spectroscopy, a non-invasive, diffuse optical method for measuring microvascular blood flow in tissue", Biomedical Optics Express, vol. 5, No. 8, Jul. 2014, pp. 2769-2784.
Varma, H.M. et al., "Speckle contrast optical tomography: A new method for deep tissue three-dimensional tomography of blood flow", Biomedical Optics Express, vol. 5, No. 4, Mar. 2014, pp. 1275-1289.
European Search Report issued by the European Patent Office dated Feb. 22, 2019 in connection with International Application No. EP 18 38 2782.

\* cited by examiner

SPECKLE CONTRAST SYSTEM AND METHOD THAT DISCRIMINATES PHOTONS PATH LENGTHS

RELATED APPLICATIONS

This application claims priority of European Patent Application No. 18 382 782.3, filed Nov. 2, 2018, the entire contents of which are hereby incorporated by reference into this application.

BACKGROUND OF THE INVENTION

Field of the Invention

The present invention is related monitoring and imaging light scatterer dynamics in turbid samples as in the case of subsurface blood flow in tissue. More particularly, the invention is directed to a new technique that aims at correcting the drawbacks present in the speckle contrast optical spectroscopy (SCOS), especially for biomedical applications, which drawbacks are the limited sensitivity to deep tissues, the optical sensor saturation at short source-detector pairs and the effect of partial volume effect that results in poor accuracy.

Description of the Related Art

The continuous probing of deep-tissue (>1 mm) blood flow is critical to the diagnosis and monitoring of many diseases. Examples include the imaging of cortical, microvascular cerebral blood flow (CBF) for stroke and other ischemic injuries, the treatment of brain injuries, and also neurodegenerative diseases such as Alzheimer's. In all these cases the state-of-the-art measurement modalities have either invasive probes (e.g. thermal dilution flowmetry, laser Doppler flowmetry), are non-continuous (i.e. single-shot) and expensive (e.g. positron emission tomography, xenon computed tomography, arterial spin labeling magnetic resonance imaging) or do not probe the microvascular blood flow (e.g. transcranial Doppler ultrasound).

Coherence optical measures have traditionally had a role in rodent stroke studies by way of the laser Doppler flowmetry. However, this method relies on single or few scattering with a limited depth penetration (<1 mm). Other speckle methods, on the other hand, monitor red blood cell movement through measures like the intensity autocorrelation function, $g_2(\tau)$, of coherent laser speckles. These techniques can also achieve depth penetration of few centimeters, thus probing parts of the cortex through the intact skull and scalp, noninvasively and continuously and at a lower instrument cost than, for example, magnetic resonance imaging.

Speckle correlation optical spectroscopy (SCOS) is a speckle method that has the following advantages: a) it provides real-time measurements of blood flow with simplified instrumentation compared to other speckle methods as diffuse correlation spectroscopy, b) it can reach tissue at a depth of few centimeters, and c) it offers a denser spatial sampling and multi-channel measurements by means of a detector array (as, for example, a CCD camera) [1, 2, 3].

However, SCOS has also important drawbacks, for example, in order to assess deep layers of a sample when the source and detector face the same side of the sample, a situation also called reflectance geometry, SCOS relies on increasing source-detector separation; this produces two unwanted effects. Firstly, the amount of light that reaches the detector decreases exponentially as the source-detector separation increases, until mainly noise is detected. To correct for this defect, it is possible to increase the injected light intensity; however, this can saturate the nearby detectors and more importantly, the safety and health of the subject, or the material integrity of the sample, can be put at risk. High dynamic range and generally more complex and expensive detectors are also needed. Secondly, the larger the source-detector separation, the more the layers of sample the light will interact with. As a consequence, the information from deep layers of the sample will be corrupted by spurious signals from the superficial layers. This is particularly detrimental in biomedical applications when assessing the red blood cells movement, so the blood flow, for example in layered body districts like the head. In this particular case, superficial layers are the scalp and skull, in which the systemic blood flow changes happening in them would mask the blood flow changes happening in the deeper layers, like the brain cortex. Hemodynamic blood flow changes in muscles or any other deep organ are also affected by this partial volume effect. Increased source-detector separations are used to increase the specificity to deep layers changes, but this can result in large detection areas and large size of the probes, which are unpractical for continuous monitoring, and again low photon count rate and low signal-to-noise ratio in the detector channels that are farther away from the source.

Thus, a system and a method are needed in order to improve sensitivity to deeper layers of a sample, while minimizing the influence of superficial layers. Additionally, a system and method are needed for obtaining deep sample information at short source-detector separation, while avoiding saturation, and easing up the requirement for high dynamic range detectors.

SUMMARY OF THE INVENTION

The present invention provides a system and method that addresses the limitations of speckle contrast optical spectroscopy (SCOS) by providing the capacity of discriminating or classifying photons according to their path length and consequently enhancing the depth specificity of the measurement in the reflectance geometry.

Differently from SCOS, the proposed invention is able to enhance the deep layers specificity of the measurements of scatterer dynamics within a sample, to reduce the partial volume effects without compromising lateral resolution, and to avoid the saturation of the sensor by extending the dynamic range of the measurement. This provides an important benefit on the monitoring of blood flow in biomedical applications; since the influence of superficial layers of tissue, mostly affecting photons with short path lengths, can be minimized by selecting the photons with long path lengths.

Reducing the partial volume effect, which is originated by not being able to separate scatterer dynamics in deep from superficial layers of a sample, may be beneficial to the efficiency of the diagnosis of diseases in various body districts. Notable examples are the breast, the thyroid, especially for early cancer detection, and probing the metabolism in the muscle. In breast, cancer exhibits higher blood flow, and this can be detected by scanning a probe or taking an image of a large area to identify "hot spots" with increased blood flow. So far, cancer diagnostic has been proven feasible only for superficial lesions. A benefit of the enhanced depth specificity of the invention can be the increase of the contrast of deep lesions allowing the diagnostic of lesions that are too deep for SCOS or DCS. In the thyroid, which is a superficial organ but still lays below few mm of skin and neck tissue, being able to selectively probe deeper layers might reduce the effects of the variability of the measurements of thyroid blood flow among different subjects. A decrease of the partial volume effect generated by the less metabolically active and reactive superficial tissue is beneficial also when studying muscles. In patients with peripheral artery disease (PAD), the more penetrating diffuse optical blood flow measurements are already proven to reflect important elements of PAD physiology that are not accessible to simply near infrared spectroscopy-based oximetry, which is plagued by even lower deep layer specificity. This invention can be used to enhance the deep layer specificity even further. One of the main limitations of blood flow-based diagnostic technique is in fact that differences in the superficial thickness of adipose tissue may introduce inaccuracies that might also account for some of the measured blood flow variability that was encountered in previous PAD studies.

Therefore, the application domain includes also the monitoring of blood flow in various tissues and organs, among other changes that may happen in the way the body interacts with light. Examples are fast optical signals detection due for example to neuronal activity. Outside the biomedical realm, the method can be applied to the study of a variety of scattering samples such as fluid flow, foam and grain dynamics. The method consist of the following steps:

directing light from a pulsed light into a sample by optical elements;
synchronizing the time between the pulse injection to sample and the detection unit;
collecting the photons that have travelled through the sample by optics, and conveying the photons of a single or a limited number of speckles from the sample to one or more detection elements;
time-tagging photons thanks to the synchronization of the detector element and/or the time-tagging electronics with the laser pulse emission;
estimating each photon time-of-flight by the difference between its time tag and the laser pulse emission;
categorizing the detected photons based on the value of the time-of-flight in a certain number of time gates;
measuring the speckle contrast for each categorized set of recorded photons intensity at the detector;
comparing measured speckle contrast iteratively to a modeled speckle contrast, which has the scatterer dynamics as free parameter. Systems for carrying out the method are also provided.

BRIEF DESCRIPTION OF THE DRAWINGS

To complete the description and provide a better understanding of the invention, a set of drawings is provided. Said drawings illustrate a preferred embodiment of the invention, which should not be interpreted as restricting the scope of the invention, but just as an example of how the invention can be carried out.

DESCRIPTION OF THE PREFERRED EMBODIMENTS

Figure 1:
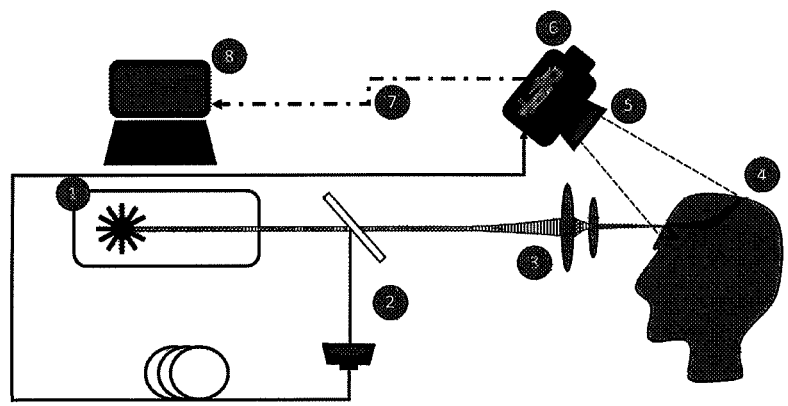
FIG. 1 shows a first embodiment of the invention.
Figure 2:
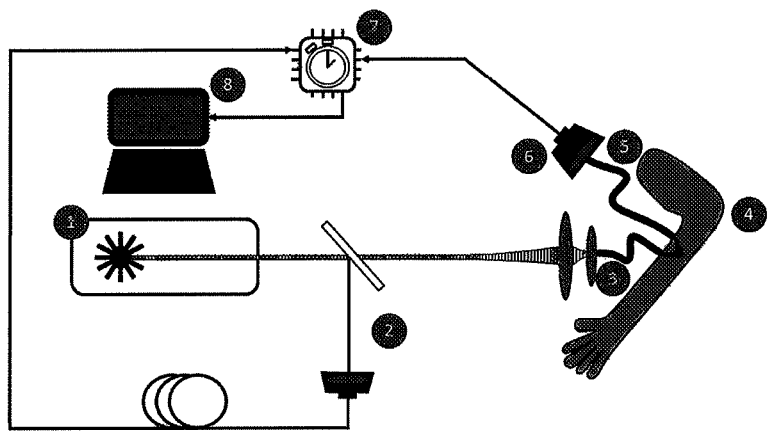
FIG. 2 shows a second embodiment of the invention.

Referring to FIG. 1, a first embodiment of the invention includes a pulsed source 1, as for example a laser, delivering pulses of light to the target medium,
a mechanism to produce a pulse synchronization (sync) trigger signal 2,
optical system to deliver the light on the sample 3,
optical system to guide light or for collection 5,
a device to detect light reemitted by the sample 6,
some timing electronics 7 and computer means 8 to process the speckle contrast and extract information on the sample dynamics, store the data FIG. 1 is the preferred embodiment of the invention. FIG. 2 represents a second proposed embodiment which constitutes an even more functional variant with multiple detector elements integrated into a single detector, as explained below.

The source produces pulses of light with a temporal length of preferably between 1 fs and 10 ns. The light source has a power (average) of preferably between 10 µW and 10 W and a coherence length between 10 µm and few meters.

A system of optical elements 3, also termed "delivering optical system", at the light output of the source, is used to collect the light from the source and inject it into the sample. This system of optical elements is usually made as a combination of one or multiple simpler optical elements, including but not limited to multi-mode or single-mode fiber optics, lenses, aperture, mirrors or any combination of them.

The sync trigger is an electronic, digital, 1-bit signal, which is as finely and accurately as possible synchronized with the laser pulses emission. For example, it is normally a logical 0 (zero) but rises to logical 1 (one) when the pulse of light is emitted and goes back to logical 0 (zero) in less time than the laser pulse period. By detecting the rising or falling edge of this signal, it is possible to recover the timing of the laser pulse emission. The signal can be produced in some cases externally, by splitting off part of the laser light of the source by means of a beam splitter and its detection later by a photodiode, as shown in FIG. 1 and FIG. 2 and marked as (2). Detection of light from the pulse at the diode raises the sync trigger from a logical 0 (zero) to logical 1 (one) for some time. In other cases, like in some commercial models of lasers, especially diode lasers, an electronic sync output is already present (not shown in the figures). When it is present, the electronic sync output can be used as the sync trigger. However, an external detector can still be beneficial because it generally results in sync triggers with more precise timing. Sync trigger rising or falling edge can be delayed by using for example connection cables of various lengths or electronic delayers, but it has still to be accurate in timing and have a small as possible time jitter, i.e. the delay has to be constant during operation. In particular, for the embodiments discussed, an external photodetector was used, and the cable length was adjusted to match the delay in the optical line.

The scope of the sync trigger for the invention is to synchronize the time of detection of photons and the emission of the pulses of light by the source. This allows ultimately to compute the time spent in the sample by each photon, also termed time-of-flight (TOF). While an electronic sync trigger is a practical solution, other means of synchronization are, for example, using a separate precise clock that keeps track of the absolute emission and detection times.

A system of optical elements, as shown in FIGS. 1 and FIG. 2 and marked as (5), termed here the optical collection system, is used to collect light that has travelled through the sample. This optical system can be made as a combination of one or multiple simpler optical elements, including but not limited to: one or more single-mode or multi-mode fiber optics, one or more lenses, one or more apertures, a more complex system of lenses and apertures like one or more photographic or cinematographic objectives, single or multiple mirrors, for example digital micro-mirror devices, or any other combination of these elements or systems. The scope of the collection system is to convey the light of a single or a limited number of speckles from the sample to one or more detection elements.

The detector element 6 is an active photodetector element, e.g. the pixel of a camera that can be for example a CCD, CMOS, or intensified camera, or a single photon avalanche diode (SPAD) or an element, also termed pixel, of a SPAD array, or a hybrid detector. Each detector element is able to generate a detectable response when it interacts with light. This process is termed detection. Detector elements are divided in:

a. Single photon counters, when they produce a detectable and accurately timed response for every photon detected,
   b. Integration counters, when they record the number of photons over a specific integration time or bin.

Note that there may exist some single photon counters that also store the number of interactions. Note also that there exists a variability of the delay in time between the light interaction and the production of a detectable response that is called time jitter. This jitter time is, for the purpose of the invention, to be kept between 1 ps and 1 ms.

In FIG. 2 we describe another preferred embodiment, where multiple detector elements are combined into an array. Non-contact deliver and collection optical systems work by using lenses and apertures as in the case of non-contact speckle imaging and detection described above (e.g. SCOS).

Time-tagging electronics (TTE) is an electronic device that compares and records in a time tag, which is a digital entry to be written in a file, the difference in time between an edge (rising or falling) of the signal generated by the detection of light in a detector element with respect to an edge of the electronic signal used for the synchronization with the pulse emission. For example, the electronic signal is the sync trigger. Time-tagging electronics can be implemented by an independent circuit, like a time-to-digital converter (TDC) or a time-correlated single photon counter (TCSPC), or a circuit that is integrated in the detector element.

The detected light is discriminated in time gates with duration $\Delta t$. A time gate is a collection of differences in time values between the time of detection of a single photon and the time at which a pulse was emitted from the source. Photons detected shortly after the pulse emission will populate the earlier time gates, while photons detected after larger delay times populate the later time gates. The difference between the time a light pulse is injected into the sample and its collection, i.e. when it emerges from the sample, is called time-of-flight (TOF) and is related to the path length of light in the sample. For a homogeneous sample (in terms of refractive index), the path length is the product of the TOF and the speed of light in the medium. In practical terms, the TOF for each photon is calculated from the measurable time difference between the generation of a detectable response in a detector element and the pulse emission time, referenced for example from a sync trigger. Both the sync trigger, or any other synchronization signal as described above, and the detectable response, can be for example electronic signals and can have fixed and measurable delays with respect to the time of light injection, and with respect to the time the light exits the sample, respectively. The difference between these delays can be precisely measured, as described below, with a system calibration. For the purpose of the invention, the duration of a time gate $\Delta t$ lasts between 1 ps and 1 ms.

Time gating is the act of considering for further processing only the light interactions that belong to a certain time interval termed gate. This can be achieved in two ways:

a) the detector element receives the sync trigger and is turned ON during just a temporal interval within the pulse period. These detectors are termed fast-gated because the time to turn ON the detector is very short. Depending on the detector element type, fast gating can be implemented by acting on the bias voltage (semiconductor detector, e.g. SPADs) or by turning on or off the intensifier in intensified CCD. For the purpose of the present invention, a fast gating detector element has transition times between 1 ps and 1 ms, and the duration of the fast gating time interval is between 100 ps and the laser pulse period. As a result, only the interactions of light with the detector elements that happen within this time interval are considered for further processing. In case the fast-gated detector elements that are also integration detector elements, this is sufficient for time gating: the time interval becomes the time gate, and this is generally the cheapest and most practical way of implementing time gating. If the fast-gated detector elements is instead a pure single photon counting detector, time-tagging electronics (TTE) devices or photon counter devices are needed as a second stage. This option is generally more expensive but also flexible because it allows an additional time gating capability of the detection events.
   b) the detector element is a single photon counter that it is ON through the whole laser pulse period. In this case, a time-tagging electronics (TTE) is mandatory in order to obtain a time tag for each light detection event. This is a middle ground between cheap fast-gated integration detector elements and fast-gated single photon counting detector elements The union of a detector element and the electronic device used for timing, either if separate or integrated together, is also termed a detection unit.

To sum up, time gating can be achieved by complementing the detector element with an electronic device (time-tagging electronics, fast gating or both) that acts in sync with source pulsed emission via the sync trigger or by having access to a referenced time synchronized with the emission of pulses of light by the source. The delay between the sync trigger and the start of the fast gating time interval can be freely adjusted by changing, for example, the sync trigger cable length or with an electronic delayer, or even by increasing or reducing the optical path length that exists before the detector.

The invention works in both, transmission and reflection mode, meaning that the invention can collect light on the same side (reflection) and/or on an opposite side (transmission) of the sample where light is delivered. In the reflection mode, the longer the time-of-flight of the photons, the deeper the photons can travel tissue [4] or in general in any turbid sample. In the embodiments here described, this property is used to enhance the depth sensitivity of the method.

Method of Time-Domain SCOS

A speckle pattern is an interference pattern of bright and dark spots, each termed speckle. It is produced when coherent light is scattered or reflected from an inhomogeneous object. For a given speckle, speckle contrast ($K^2$) is defined as the variance ($\sigma_{I,T}$) over the mean square of the time-varying speckle intensity I $$\kappa^2 = \frac{\langle I(t)^2 \rangle_T - \langle I(t) \rangle_T^2}{\langle I(t) \rangle_T^2} = \frac{\sigma_{I,T}}{\langle I(t) \rangle_T^2}$$

where $\langle I(t) \rangle_T$ represents the time average of the detected intensity over the exposure time T.

The speckle contrast is readily measured by the apparatus described above, for one or more time gates separately. In order to extract information, a model that relates the time-domain, gated, speckle contrast, to the movement of the light scattering particles in the sample, is needed.

The time-domain speckle contrast can be first related to the normalized auto-correlation function of the electric field of the detected light $c_e(\tau)$, where $\tau$ is the correlation time, as $$\kappa^2 = \frac{2\beta}{T} \int_0^T \left(1 - \frac{\tau}{T}\right) [c_e(\tau)]^2 d\tau \quad (1)$$

$c_e(\tau)$ is given by the integral of the contributions of all the possible paths of length s of the detected light in the sample, weighted on the probability of each path length f(s). The latter depends on the optical properties (scattering and absorption coefficients, $\mu_s$ and $\mu_a$) of the medium and can be computed numerically or, given some simplifying approximation to the radiative transport, through the solution of the time-resolved photon diffusion equation (see below). The normalized electric field auto-correlation can instead be written as $$c_e(\tau) = \partial_{s0}{}^{s1} f(s) c_e^{sgl}(\tau, s) ds \quad (2)$$

In this model equation, $c_e^{sgl}$ can now be readily written as a statistical average of the electric field E(t) at the detector location $$c_e^{sgl}(\tau, s) = \frac{\langle E^*(t) E(t+\tau) \rangle_s}{\langle E^*(t) E(t) \rangle_s} \quad (3)$$

Equation (3) is the electric field autocorrelation when considering only the contributions of the photons that underwent a single path of length s among the scatterers of a turbid medium. The bracket $\langle \cdot \rangle_s$ represents an average over an ensemble of different path lengths of the same length s.

To infer the single path auto-correlation or the light transport model, some insight on the light-turbid sample interactions must be given. Tissue is an example of a turbid medium, which means that light can be either absorbed or (more likely) elastically redirected (scattered). While in dynamic turbid media any moving scattering particle can be in theory probed, it has been shown that in living perfused tissue the main moving scattering particles are the red blood cells [7]. It is, however, possible to monitor the changes in the refraction that are caused by the dynamics of any microscopic membrane or, more in general, discontinuity of the optical refractive index, that is able to scatter light. The same methods described here apply to scattering dynamics other than blood flow. Striking examples are, apart from the red blood cells, lipid micelles and the membranes of neurons and, outside the biomedical realm, the dynamics of fluid, foams and grains flow.

Along any of its paths in the turbid sample, light is redirected (scattered) multiple times. This can be seen as a stochastic process with a typical length scale given by the mean free path $l = 1/\mu_s$, where $\mu_s$ is the scattering coefficient. Due to the anisotropy of the scattering (light is predominantly redirected towards the forward direction), the direction of the photons is generally not independent from the original direction after each scattering event. However, for a high number of scattering events along a path length, like in most experiments in tissue, the transport mean free path length $l^* = 1/\mu_s'$ can conveniently be defined as the typical length after which the direction of propagation of the photons is randomized. In this formulation $\mu_s' = (1-g)\mu_s$ is termed reduced scattering coefficient, and $g \in (-1,1)$ is a constant that in general for tissue assumes values $g > 0.7$, which means highly anisotropic, forward-directed scattering. The transport mean free path $l^*$ is in the order of 100 μm, while for a typical experiment, photon path lengths in tissue are in the order of a few centimeters up to a few meters. Light therefore quickly loses its initial direction of propagation as it travels through tissue, with $l^*$ being the typical length after which the direction of propagation of the photons is randomized.

Under certain conditions, the summation of the scattered electric fields from each scattered particle can be approximated as a random walk in the complex plane given by the sum of single scattering contribution. In the single scattering regime, when light is detected after interacting just once with one of the scatterers of the sample, the electric field auto-correlation function is an exponentially decaying function with respect to the correlation time T. The decay rate is proportional to the scalar dot product of the scatterer displacement, i.e. $\Delta r(\tau) = r(t+\tau) - r(t)$ (here r(t) is the position of the scattering particle at time t), over a certain time interval $\tau$, and the momentum transferred by the photon, q $$c_e(\tau) = \exp(i\omega\tau) \langle \exp(iq \cdot \Delta r(\tau)) \rangle$$

In this formula $$\omega = \frac{2\pi}{\lambda'}$$

is the oscillating frequency of the electric field, being $\lambda'$ its wavelength in the medium.

In multiple scattering regime, $c_e^{sgl}(\tau, s)$ is proportional to the ensemble average of the product of the normalized electric field autocorrelation of all the scattering events (of index j) along paths of length s $$c_e^{sgl}(\tau, s) = \exp(i\omega\tau) \langle \Pi_j \exp(iq_j \cdot \Delta r_j(\tau)) \rangle_s \quad (4)$$

When light scatterers in the turbid sample diffuse as Brownian diffusers or, as it has empirically been shown, when the scatterers are red blood cells in tissue, the particle displacement $\Delta r$ is distributed as a Gaussian variable, this further simplifies to $$c_e^{sgl}(\gamma, \tau, s) = e^{-\gamma\tau s} \quad (5)$$

where $\gamma = 2\mu_s' k_0^2 \alpha D_B$ is a parameter that describes the decay rate of the autocorrelation function. In this equation, $k_0^2$ is the square of the wavenumber of light in the medium, $\alpha$ is the fraction of moving scatters, and $D_B$ is the Brownian diffusion coefficient. For blood flow in tissue, since the parameter α is difficult to measure in practice, a combined parameter called blood flow index (BFI=αD$_B$) can be used instead.

The integral in equation (2) is carried out between the extremes s$_0$ and s$_1$, that are the minimum and maximum path lengths of photons in the sample that can be detected within a gate of duration Δt. Under the approximation of constant average index of refraction, n:

$$v\Delta t = s_1 - s_0 \qquad (6)$$

where v=c/n is the speed of light in the medium (speed of light in vacuum over the medium's refractive index). Being able to change the duration of the gate and its delay with respect to the pulse emission time, we can selectively consider any subset of the possible photon path lengths [s$_0$, s$_1$] and this ultimately allows achieving the enhanced sensitivity at a certain depth. In reflectance geometry, when source and detector are on the same side of a semi-infinite slab of a sample, photons with greater path length and higher detected time-of-flight (termed late photons) will statistically probe deeper regions of the sample. Conversely, photons with lower detected time-of-flight (termed early photons) will be most likely dwelling in the most superficial regions.

A definition of time-domain-speckle contrast optical spectroscopy according to the invention can be derived by inserting equations (2) and (5) in (1) to obtain:

$$\kappa^2 = \frac{2\beta}{T}\int_0^T \left(1 - \frac{\tau}{T}\right)\left[\int_{s_0}^{s_1} R(s)e^{-\gamma\tau s}ds\right]^2 d\tau \qquad (7)$$

The probability distribution of the photon path length f(s) can be computed from theory. Since the path length is the time-of-flight of photons multiplied by the speed of light, f(s) can be obtained from:

$$f(s) = \frac{R\!\left(\rho, \Delta t = \frac{ns}{c}\right)}{\int_{s_0}^{s_1} R\!\left(\rho, \Delta t = \frac{ns}{c}\right)ds}$$

where R is the time-resolved reflectance solution of the diffusion equation with appropriate boundary conditions. In particular, for an extrapolated boundary condition, R is given by [5]:

$$R\!\left(\rho, \Delta t = \frac{ns}{c}\right) = \begin{cases} \frac{1}{(4\pi Dv\Delta t)^{3/2}} e^{-\mu_a v \Delta t} e^{-\frac{\rho^2}{4Dv\Delta t}} \left[\left(\frac{0.15 z_0}{\Delta t} + 0.11v\right)e^{-\frac{z_0^2}{4Dv\Delta t}} + \left(\frac{0.15(z_0 + 2z_b)}{\Delta t} - 0.11v\right)e^{\wedge -\frac{(z_0 + 2z_b)^2}{4Dv\Delta t}}\right] & s_0 < v\Delta t < s_1 \\ 0 & \text{otherwise} \end{cases} \qquad (9)$$

where D=v/3μ$_s$' is the photon diffusion coefficient, μ$_a$ is the absorption coefficient, z$_0$=1/μ$_s$' is the location of an isotropic source inside the medium, and $$z_b = \frac{2}{\mu_s'}\frac{1 + R_{\mathit{eff}}}{3(1 - R_{\mathit{eff}})}$$

is the location of the extrapolated boundary condition. Here R$_{\mathit{eff}}$ is the effective reflection coefficient introduced to account for the index mismatch between the sample and air. . For a typical index of refraction of the tissue of n=1.4 in air then R$_{\mathit{eff}}$=0.5295.

The model for the speckle contrast obtained solving equations (7) to (9) is compared with the time-domain speckle contrast, computed for each detector element, limited to the light interactions that happened within a certain time gate Δt. Every T$_{min}$ seconds the light intensity for all the time gates considered is read by summing the number of light interactions within that time gate on the detector element; then this same counter is reset. T$_{min}$ can be any multiple of the laser pulse period Δt. T is the exposure time and is a multiple of T$_{min}$. The formula for the computation of the measured speckle contrast then is [6]:

$$\kappa(T) = \frac{\sigma_{I,T}}{\langle I \rangle_T} \qquad (10)$$

The time-domain speckle contrast can be computed spatially or temporally.

In the former, the mean and standard deviation are computed in small spatial windows of the laser speckle raw images. The size of the spatial window is crucial since too few pixels could compromise the statistics, and too many pixels sacrifice the spatial resolution. Usually these spatial windows correspond to squares of 5×5 or 7×7; however, the spatial window size can change depending on the application. Additionally, a square with sides of an odd number of pixels is usually selected because the speckle contrast can be assigned to the central pixel, but by no means does this restrict choosing an even number of pixels for the side of the square.

The temporal speckle contrast is computed by using a set of statistically independent frames, the mean and standard deviation are computed accordingly. The minimum number of frames should be higher than one frame, and the maximum number of frames is provided by the minimum admissible temporal resolution.

In general, multi-exposure data can be obtained by defining T$_i$=nT$_{min}$ with T$_n$≤τ$_d$ where n is an integer and τ$_d$ is the decorrelation time, which is the time required to obtain two independent speckle samples. T$_{min}$ can be in the range 0.1≤T$_{min}$≤1 μs, 1≤T$_{min}$≤10 μs, 10≤T$_{min}$≤100 μs, 0.1≤T$_{min}$≤10 ms, 10≤T$_{min}$≤100 ms, 100≤T$_{min}$≤1000 ms. In particular, for the preferred embodiment, T$_{min}$ was set to 50 μs. τ$_d$ can be comprised in the range 1≤τ$_d$≤100 μs, 0.1≤τ$_d$≤1 ms, 1≤τ$_d$≤5 ms, 5≤τ$_d$≤50 ms, 50≤τ$_d$≤100 ms, 100≤τ$_d$≤1000 ms. In particular, for the preferred embodiment τ$_d$=5 ms. Finally, the exposure time T can be comprised in the range 5≤T≤50 μs, 0.05≤T≤5 ms, 5≤T≤50 ms, 50≤T≤100 ms, 100≤T≤1000 ms. In particular, for the preferred embodiment the following exposures were used: T={50, 100, 200, 400, 600, 800, 1000, 1200, 1400, 1600, 1800, 2000, 3000, 4000, 5000, 6000, 7000, 8000, 9000, 10000} μs.

An optimization algorithm minimizes the squared norm of the difference between the measured and computed speckle contrast (objective function) until an optimum value for BFI ($\alpha D_b$) is found, this is expressed mathematically as $$\min_{BFI} \|\kappa^2 - \kappa_{meas}^2\|_2 \quad (11)$$

where $\eta_{meas}$ refers to the measured speckle contrast and $\eta$ is the computed speckle contrast obtained by solving equations (6) to (9). The optimization function in equation (11) can be solved using appropriate methods such as, but not limited to, least-squares-based methods, gradient-based methods, or simplex-based methods. The stopping criterion can be based on the number of iterations or on a tolerance error. In particular, for the embodiments here discussed, the algorithm stopped when the difference of the squared norm, represented in equation (11) as $$\|x\|_2 = \sqrt{\Sigma(x_i^2)},$$

where the index i runs over the measured speckle contrasts, between consecutive iterations, was less than 0.1%. Once the algorithm has stopped, the optimum value forum for BFI is reported in a display as an indicator of the dynamics of the scatterers in the sample. As a result of the time gating, this index will have enhanced depth sensitivity with respect to standard SCOS.

Since the time-tagging process described above to ultimately measure the time-of-flight of the photons depends critically on optical and electronic delays, a calibration step is needed prior to the measurement. This is done by turning the deliver toward the collection optics systems, i.e. by removing the sample. In this way, the detected light intensity is the (attenuated) pulsed light from the source. By adjusting the time gate delay with respect to the pulse emission, which can be done operatively by increasing the space travelled by laser light, e.g. with three or more mirrors, the light intensity detected (/) shall increase from the detector element and electronics noise floor IN to a maximum IM. This maximum value shall be kept under saturation values by adding filters to the path to decrease light intensity if needed. The zero delay time to is defined as the delay time at which $$I(t_0) = \frac{(I_M - I_N)}{2}.$$

Or alternatively, when the intensity reaches a peak.

The calibration of the delay value is much simplified when using single photon counters and time-tagging electronics: in this case, the intensity at each precisely measured delay time of the detection with respect to the pulse emission can be plotted as a histogram, resulting in a bell-shaped curve rising from the detector element noise floor for each detector element. The width of this bell-shaped curve, also called instrument response function, depends on various factors like the laser pulse duration, the non-deterministic time jitter of the detector element and the non-deterministic time jitter of the time-tagging electronics, etc. The zero time delay or to is defined in this case as the delay corresponding to the peak of the bell-shaped histogram.

Figure 3:
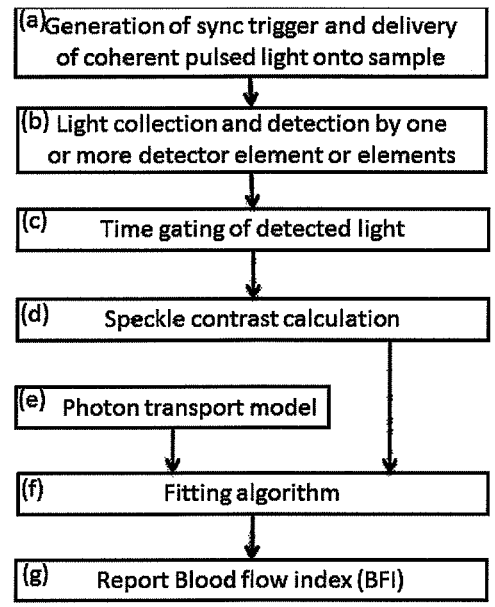
FIG. 3 is a flow chart of the method of the invention.

FIG. 3 is a block diagram of the method of the invention. The method steps are as follows:

(a) Photons from a pulsed laser (785 nm wavelength, 100 MHz pulse frequency, 30 mW power) are injected into the sample after traveling through a multi-mode fiber optics of 200 μm diameter. For each emitted pulsed, a sync trigger signal is produced by an external photo-diode receiving a small portion (<5%) of the light from the laser. The sync trigger was a transistor-transistor logic (TTL, 0 volts is interpreted as low level or 0, 5 volts is high level or 1) digital signal; digital high level or 1 lasts 2 ns.

(b) Light that has travelled through the sample is collected by a single mode fiber (at a short separation of 2.85 mm from the source fiber) that convey the light of a single speckle from the sample to one detection element, in this particular case a fast-gated SPAD. The fast-gated SPAD ON temporal window is 4 ns. The fast-gated SPAD received the sync trigger, and its delay was set to reject the early arriving photons, arriving between 0 and 512 ps, which are particularly abundant at this short separation and can saturate a non-time-gated detector. Photon counts from the fast-gated SPAD were time-tagged and saved to a file by a Pico Harp 300 time-correlated single photon counter device that was also receiving the electronic sync trigger.

(c) The light intensity within a certain time gate (Δt) is computed by counting the corresponding time tags. Δt can be freely adjusted. In the described embodiment we considered a Δt equal to the pulse period since time-gating is already implemented in this case by the fast-gated SPAD (Δt=4 ns). Every $T_{min}$ seconds the integrated light intensity is read, and the element is reset. $T_{min}$ can be any multiple of the laser pulse period Δt. In particular, for the preferred embodiment, T={50, 100, 200, 400, 600, 800, 1000, 1200, 1400, 1600, 1800, 2000, 3000, 4000, 5000, 6000, 7000, 8000, 9000, 10000} μs.

(d) The time-domain speckle contrast (η) is calculated as the ratio of the standard deviation (σ) to the mean intensity ($\langle I \rangle$) [6], both computed with only the light that belongs to each time gate Δt:

$$\kappa(T) = \frac{\sigma(T)}{\langle I(T) \rangle}$$

where T is the exposure time and is a multiple of $T_{min}$. For every exposure time and every Δt considered, the value of the speckle contrast in (c) is compared with the model through a fitting procedure. This computation can be implemented in a PC or any other system like a field-programmable gate array (FPGA) or microprocessor.

(e) The fitting procedure to estimate the BFI can be implemented in a PC. Such a fitting procedure can be iterative or non-iterative. In particular, for the preferred embodiment, an iterative procedure was employed, and the search of the optimum value was stopped when the error in BFI between successive iterations was less than 0.1%, and the value of the objective function in equation (11) was less than 0.01% in comparison to the previous iteration.

(f) The computed BFI is reported in a graph along with the one at the same times by standard SCOS on the free-running detector.

Experimental Demonstration

We demonstrated the invention by computing rBFI changes due to an arterial arm cuff occlusion test on an adult healthy human subject (female, 26-years-old) and comparing the results between the method of the invention (time-domain SCOS) and the standard SCOS.

Instrumentation

A Ti:Sapphire laser in the active mode-locked regime at the wavelength λ=785 nm was used as a pulsed source of the invention. The pulse repetition rate was 100 MHz and the pulse width 350 ps at full width half maximum (FWHM). A small fraction (<5%) of its light was split off to a photodiode, whose output generated the synchronization signal, while the rest of the light was delivered to the tissue using a multimode fiber. Single mode fibers (cutoff at 730 nm) were instead used for light collection.

Correlation curves from an electronic correlator connected to a SPAD detector in free-running mode, which was detecting light from a fiber positioned on the skin at $\rho=12$ mm from the source fiber, were analysed, as if the source were continuously emitting, with the standard SCOS model. This way the SCOS-derived BFI was measured for comparison.

A second SPAD was gated in order to detect the photons in a few nanoseconds time interval, or gate, synchronized with the delayed photodiode signal. The data generated by this other detector was used for TD-SCOS analysis. The detector fiber for the gated SPAD was located at a much closer, $\rho=2.85$ mm, quasi-null separation from the source fiber on the skin.

The gated SPAD, with nominally 100 ps timing jitter, was connected to a TCSPC (Pico Harp 300, PicoQuant, Berlin, Germany), which recorded in a file the arrival time (time tags) of the photons that it detected: for each detected event, the TCSPC recorded the time delay with respect to the laser synchronization signal with 25 ps resolution and the overall (laboratory) arrival time with a coarser 20 ns resolution.

The gated SPAD was ON for 4 ns (this is the temporal interval or gate) and synchronized with the laser pulse repetition frequency. By acquiring the laser pulse (no sample) directly, we adjusted the delay until the rise time of the gate was 512 ps after the peak of the pulse.

Experimental Protocol

The three fibers (one source, two detectors), embedded in a black foam matrix to shield ambient light were gently placed on the brachioradialis muscle of a healthy subject. Maximum permissible exposure limit for human skin (30 mW) was met at the source fiber. The arm cuff occlusion protocol consisted of inflating above the arterial pressure of the subject, a pneumatic cuff placed just under the ipsilateral (to the probe location) shoulder joint. The cuff remained inflated for 3 minutes, blocking the blood flow to the probed tissue. After this, the air in the cuff was abruptly released, causing the blood to flow back to the arm.

Standard SCOS Model

A model that describes the standard SCOS method can be obtained by using equation (1) with the integration limits defined as $s_0=0$ and $s_1=\infty$. Note that this model is the same as for a continuous light source.

Signal Processing And Fitting Procedure

To obtain time-domain SCOS data according to the invention, the arrival time of photons provided by the invention was taken into account to bin the number of photons at different exposure times; then for each exposure time, the speckle contrast was computed. The exposure values used were T 32 {50, 100, 200, 400, 600, 800, 1000, 1200, 1400, 1600, 1800, 2000, 3000, 4000, 5000, 6000, 7000, 8000, 9000, 10000} μs. The speckle contrast was computed temporally by employing a set of a hundred frames to calculate the standard deviation and mean intensity. Eq. (10) was used to calculate the measured speckle contrast obtained by the invention, while the modelled speckle contrast was computed from equation (7) to (9). Then, an optimization algorithm was used to minimize the difference between the two sets of data in order to find the BFI. At the same time, the parameter β was estimated during the fitting process with a mean value of 0.26.

On the other hand, SCOS measurements were calculated using equation (1) where the data for $c_e(\tau)$ was obtained from the hardware electronic correlator by using the Siegert relation $$c_I(\tau) = \frac{\langle I(t)I(t+\tau)\rangle}{\langle I(t)\rangle^2} = 1 + \beta|c_e(\tau)|^2$$

on the intensity correlation $c_I(\tau)$ that the electronic correlator renders. Here β is a parameter that depends on the optics and the coherence of the laser and we used β=0.21.

The exposure values used were T={50, 100, 200, 400, 600, 800, 1000, 1200, 1400, 1600, 1800, 2000, 3000, 4000, 5000, 6000, 7000, 8000, 9000, 10000} μs. The BFI was calculated from an optimization algorithm that minimized the difference between the measured speckle contrast data and the modelled speckle contrast data.

The same MATLAB function and fitting parameters were used as in the previous paragraph. In this manner, it is possible to compare the BFI obtained from SCOS and time-domain SCOS.

Results

Figure 4:
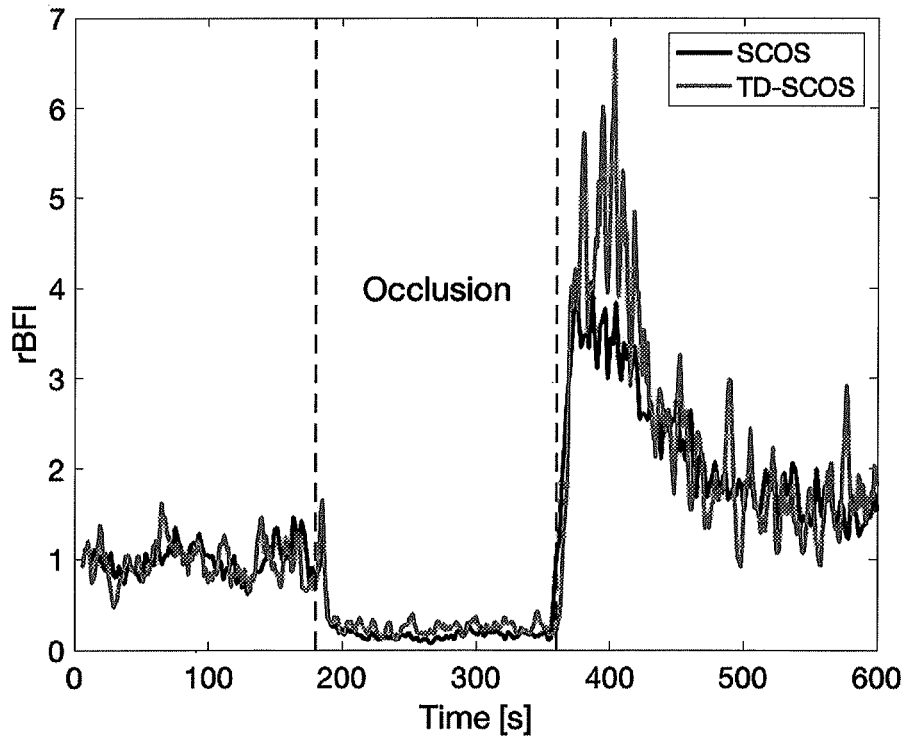
FIG. 4 is a graph showing the advantages of the new method in comparison to the state of the art.

Results are shown in FIG. 4 where the BFI has been normalised to the first 100 s of the experiment, i.e., relative BFI (rBFI). The graph shows the time series of the rBFI derived from both techniques, before, during and after the arm cuff occlusion tests. It has been demonstrated that as the source-detector separation increases, measurements are more sensitive to deeper tissue, in this case muscle, and therefore the relative change of the magnitude of reactive hyperaemia (blood flow overshot after occlusion) also increases. However, the gating technique also allows selecting the photons that have travelled deeper in tissue using quasi-null separation. This is demonstrated in FIG. 4 where the overshoot in the hyperaemic is ~33% higher than that of the traditional approach, albeit some increase in the noise. One more significant difference is the faster decay captured by the invention, which is also a characteristic of deep tissue, i.e., the gated, quasi-null-separation measurement probes selectively deeper into the more metabolically active and reactive muscle tissue, as was observed in multi-distance measurements.

As it is used herein, the term "comprises" and derivations thereof (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.) to be within the general scope of the invention as defined in the claims.

The application domain is not limited to blood flow. In a broader sense, the method and system described herein are related to the measurements of other dynamic properties of tissues that alter the laser speckle statistics such as the infra-slow and fast optical scattering signals due to morphological changes, e.g. neuronal swelling, or other scattering samples such as fluid flow, foam and grain dynamics.

REFERENCES

[1] Valdes, C. P., H. M. Varma, A. K. Kristoffersen, T. Dragojevic, J. P. Culver., T. Durduran. "Speckle contrast optical spectroscopy, a non-invasive, diffuse optical method for measuring microvascular blood flow in tissue." *Biomed Opt Express* 5, 2769-2784 (2014).

[2] Varma H M, Valdes C P, Kristoffersen A K, Culver J P and Durduran T (2014), "Speckle contrast optical tomography: A new method for deep tissue three-dimensional tomography of blood flow." *Biomed. Opt. Express Vol.* 5(4), pp. 1275-1289.

[3] T. Durduran; C. Valdes; A. Kristoffersen; H. Varma; J. Culver , Speckle contrast optical tomography, U.S. Pat. No. 9,538,926B2, European patent EP2888994A1, Priority Date: Dec. 26, 2013.

[4] Martelli, F., Binzoni, T., Pifferi, A., Spinelli, L., Farina, A., & Torricelli, A. (2016). There's plenty of light at the bottom: statistics of photon penetration depth in random media. Scientific Reports, 6, 27057. Retrieved from http://dx.doi.org/10.1038/srep27057

[5] Wang R K, Wickramasinghe Y A. Fast algorithm to determine optical properties of a turbid medium from time-resolved measurements. Appl Opt. 1998; 37(31): 7342-7351.

[6] Bandyopadhyay R, Gittings A S, Suh S S, Dixon P K, Durian D J. Speckle-visibility spectroscopy: A tool to study time-varying dynamics. Rev Sci Instrum. 2005; 76(9).

[7] Durduran, T., Choe, R., Baker, W. B., & Yodh, A. G. (2010). Diffuse optics for tissue monitoring and tomography. Reports on Progress in Physics, 73(7), 76701.

The invention claimed is:

1. A speckle contrast optical spectroscopy system for discriminating photons based on their path length in a sample, the system comprising:
   a coherent pulsed light source for producing light pulses with a temporal length of between 1 fs and 10 ns;
   a time-gated detector;
   a means for synchronizing time between the source and the time gated detector, the detector being configured for a transition time between 1 ps and 1 ms and a duration of a gating time interval between 100 ps and the laser pulse period;
   an optical means for directing the light pulses towards a sample;
   an optical means for collecting the light once it has travelled the sample and directing it towards the time-gated detector; and
   a computer means for calculating the speckle contrast from the collected photons and for resolving the photons in time.

2. The speckle contrast optical spectroscopy system according to claim 1 wherein the means for producing a synchronized signal are a beam splitter and a photodiode, a laser or a clock.

3. The speckle contrast optical spectroscopy system according to claim 1 wherein the detector is adapted to be turned on and off at a time-scale that allows to accept or to reject predefined photon path lengths.

4. The speckle contrast optical spectroscopy system according to claim 1 wherein the time-gated detector is a free running detector element with a time-tagging electronics, or a fast-gated detector element, or a fast-gated detector provided with a time-tagging electronics.

5. A method for discriminating photons based on their path length in tissue, the method comprising the steps of:
   directing light from a pulsed light source into a sample by optical elements;
   synchronizing time between pulse injection to sample and one or more detection elements;
   collecting photons that have travelled through the sample by optics, and conveying the photons of a single or a limited number of speckles from the sample to the one or more detection elements;
   time-tagging the photons by synchronization of the one or more detection elements and/or time-tagging electronics with laser pulse emission;
   estimating each photon time-of-flight by a difference between its time tag and the laser pulse emission;
   categorizing the detected photons based on a value of time-of-flight in a certain number of time gates;
   measuring speckle contrast for each categorized set of recorded photons intensity at the one or more detection elements; and
   comparing the measured speckle contrast iteratively to a modeled speckle contrast, which has scatterer dynamics as free parameter.

6. The speckle contrast optical spectroscopy system according to claim 2 wherein the detector is adapted to be turned on and off at a time-scale that allows to accept or to reject predefined photon path lengths.

7. The speckle contrast optical spectroscopy system according to claim 2 wherein the time-gated detector is a free running detector element with a time-tagging electronics, or a fast-gated detector element, or a fast-gated detector provided with a time-tagging electronics.

8. The speckle contrast optical spectroscopy system according to claim 3 wherein the time-gated detector is a free running detector element with a time-tagging electronics, or a fast-gated detector element, or a fast-gated detector provided with a time-tagging electronics.

9. The speckle contrast optical spectroscopy system according to claim 6 wherein the time-gated detector is a free running detector element with a time-tagging electronics, or a fast-gated detector element, or a fast-gated detector provided with a time-tagging electronics.

10. A method for discriminating photons based on their path length in tissue, the method comprising the steps of:
    directing by optical elements light towards a sample from a pulsed light source with pulses having a temporal length of between 1 fs and 10 ns;
    synchronizing time between pulse injection to sample and one or more detection elements;
    collecting by optics photons that have travelled through the sample, and conveying the photons of a single or a limited number of speckles from the sample to the one or more detection elements;

time-tagging the photons by synchronization of the one or more detection elements or time-tagging electronics with laser pulse emission, where a transition time is between 1 ps and 1 ms, and a duration of a gating time interval is between 100 ps and a laser pulse period;

estimating each photon time-of-flight by a difference between its time tag and the laser pulse emission;

categorizing the detected photons based on a value of time-of-flight in a certain number of time gates;

measuring speckle contrast for each categorized set of recorded photons intensity at the one or more detection elements; and comparing the measured speckle contrast iteratively to a modeled speckle contrast, which has scatterer dynamics as free parameter.

* * * * *